United States Patent [19]

Bird et al.

[11] 4,238,421

[45] * Dec. 9, 1980

[54] PRODUCTION OF HEXANITROSTILBENE WITH PH CONTROL

[75] Inventors: Roger Bird, Swindon; Allen E. Webb, Waltham Abbey, both of England

[73] Assignee: The Secretary of State for Defence in Her Britannic Majesty's Government of the United Kingdom of Great Britain and Northern Ireland, London, England

[ * ] Notice: The portion of the term of this patent subsequent to Dec. 9, 1997, has been disclaimed.

[21] Appl. No.: 17,974

[22] Filed: Mar. 6, 1979

[30] Foreign Application Priority Data

Mar. 7, 1978 [GB] United Kingdom ................ 9077/78

[51] Int. Cl.$^3$ .............................................. C07C 79/10
[52] U.S. Cl. .................................................... 568/931
[58] Field of Search ......................................... 260/645

[56] References Cited

U.S. PATENT DOCUMENTS

| | | | |
|---|---|---|---|
| 3,505,413 | 4/1970 | Shipp | 260/645 |
| 4,085,152 | 4/1978 | Salter et al. | 260/645 |

Primary Examiner—Deborah L. Kyle
Attorney, Agent, or Firm—Stevens, Davis, Miller & Mosher

[57] ABSTRACT

The yield of hexanitrostilbene from the reaction of 2,4,6-trinitrotoluene and an alkali metal or alkaline earth metal hypochlorite, in an aqueous organic solvent, is improved by adjusting the pH of the reaction mixture to within the range 9.5 to 11.0 and then maintaining the pH within that range by the progressive addition of an alkali metal hydroxide. The pH is preferably kept above 9.75, especially from 10 to 10.5.

In a preferred embodiment, 2,4,6-trinitrotoluene is contacted with aqueous sodium hypochlorite (containing from 4 to 10% (w/v) chlorine) in tetrahydrofuran-methanol. After an initial reaction period of between 0.5 to 3 minutes, an inorganic acid, especially sulphuric or hydrochloric acid, is added to the reaction mixture to bring its pH within the required range, and then an alkali metal hydroxide, especially sodium or potassium hydroxide, is added continuously to maintain the pH within that range. The controlled reaction proceeds for 1 to 2 hours at −5° to 25° C., preferably 10° to 16° C. Well-known methods of isolation then afford hexanitrostilbene in yields of about 50%.

12 Claims, No Drawings

PRODUCTION OF HEXANITROSTILBENE WITH PH CONTROL

The present invention relates to the production of 2,2',4,4', 6,6',-hexanitrostilbene.

U.S. Pat. No. 3,505,413 describes a process for the production of 2,2',4,4',6,6'-hexanitrostilbene which comprises reacting in an organic solvent, 2,4,6-trinitrotoluene with an alkali metal or alkaline earth metal hypochlorite. U.S. Pat. No. 4,085,152 describes and claims an improvement thereon wherein the yield is increased by subsequently adding a nitrogenous base to the reaction mixture. The base typically is an organic amine or, to counteract the base released in the process, an amine hydrochloride. These materials are unpleasant to handle and although their presence is beneficial to the reaction in terms of yield, an alternative to their use has been sought.

Accordingly the present invention avoids the use of nitrogenous base and instead provides a process for the production of 2,2',4,4', 6,6'-hexanitrostilbene which comprises contacting, in an aqueous organic solvent, 2,4,6-trinitrotoluene with an alkali or alkaline earth metal hypochlorite and at least after an initial reaction period, adjusting the pH of the reaction mixture to within the range 9.5 to 11.0, and then maintaining the pH of the reaction mixture within that range by the progressive addition of an alkali metal hydroxide. The pH is preferably kept above 9.75, especially from 10 to 10.5.

The initial reaction period will, as explained in U.S. Pat. No. 4,085,152, normally be within the range 0.5 to 3 minutes. The aqueous organic solvent should preferably contain 40-50% (by weight) of water. In general the major proportion of the water content will be provided by an aqueous hypochlorite solution and an aqueous solution of alkali metal hydroxide, although water may also be introduced with, for example, the organic component. The organic component of the solvent may, for example, be dioxan, diglyme, or acetonitrile or mixtures thereof, but is preferably a mixture of tetrahydrofuran with another solvent especially methanol.

As the initial (rapid) reaction of the hypochlorite with the trinitrotoluene to give trinitrobenzyl chloride releases hydroxide ions it has been found that in order to obtain an optimum yield, acid should be added at this stage to give a pH within the required range. Preferably the acid is an inorganic acid such as sulphuric or hydrochloric acid. The pH is then maintained during the subsequent (slow) conversion of the trinitrobenzyl chloride to the hexanitrostilbene product (which process takes up hydroxide ions) by progressive addition of alkali metal hydroxide. In this way the pH may be kept at or around the optimum value for the reaction throughout its course. The preferred alkali metal hydroxides are common commercially available reagents such as sodium or potassium hydroxide.

In one technique for carrying out the process according to the invention the reactants, 2,4,6-trinitrotoluene and the alkali or alkaline earth metal hypochlorite, are mixed in an aqueous organic solvent in a reactor. Acid is run into the reactor effluent to bring its pH down to the desired level and the whole mixture is drained into a stirred tank. The pH of the liquid in the tank can be checked by means of a suitable electrode and alkali metal hydroxide can be run into the tank as required to compensate for the increasing acidity of the reaction mixture caused by the progressive conversion to hexanitrostilbene product.

It will be apparent that as the final reaction to hexanitrostilbene nears completion the rate of addition of alkali metal hydroxide which is necessary to ensure a constant pH will also decline and the pH will cease to change after completion of the reaction. In practice due to the slowness of the reaction it may be preferred to stop the process somewhat before the reaction is fully complete. A reaction time of from one to two hours has been found to be normally suitable.

The entire reaction is preferably carried out at a temperature within the range $-5°$ to $25°$ C., most preferably from $10°$ to $16°$ C. After completion of the reaction, the suspension obtained is filtered to separate the product. This may be washed with acetone and water (or with aqueous acetone) to remove impurities. Yields of up to about 50% of hexanitrostilbene are obtainable by this process.

The process of the invention will now be further described by way of example, by reference to some specific procedures, using apparatus similar to that illustrated in U.S. Pat. No. 4,085,152.

EXAMPLES 1 to 6

Using aqueous sodium hypochlorite with 4.5% w/v free chlorine as the hypochlorite reactant and a mixture of THF/methanol at 2:1 by volume as the solvent, a series of preparative reactions were carried out at different pH levels.

500 g of trinitrotoluene was dissolved in 6.38 liter of solvent and this solution was mixed with 4.5 liter of the hypochlorite feedstock in a stirred continuous reactor fitted with a cooling coil to remove the heat of reaction. The residence time in the reactor was of the order of 1.5 minutes. The pH of the reactor effluent was on average about 12. The effluent was run into a stirred vessel, dilute (25%) sulphuric acid being added to the effluent in order to bring its pH down to the desired level. The pH was maintained at this chosen value throughout the subsequent reaction in the stirred vessel by the progressive addition of sodium hydroxide solution (1.5 N). The pH was tested by a pH meter with combined glass electrode. The temperature in the reactor was maintained throughout at $11.5°\pm0.2°$ C.

After standing the mixture for a period of 90 minutes and acidifying, the product in suspension was filtered off, washed with acetone and then water, dried and weighed. The results obtained are given in the Table.

TABLE

| Example No | pH | Yield (% theoretical) |
|---|---|---|
| 1 | 9 | 13 |
| 2 | 9.5 | 30 |
| 3 | 10 | 47.7 |
| 4 | 10.5 | 46.6 |
| 5 | 11 | 39.7 |
| 6 | 12 | 26.7 |

By interpolation it is found that a maximum yield (48.5%) should be obtained with the above described materials and procedures if the pH of the reaction mixture in the conversion stage were maintained at a value of 10.2 throughout, this has been confirmed experimentally.

It will readily be appreciated that by doing similar sets of runs, the optimum pH for other reactant/solvent conditions may be likewise established.

We claim:

1. A process for the production of 2,2',4,4',6,6'-hexanitrostilbene which comprises contacting, in an aqueous organic solvent, 2,4,6-trinitrotoluene with an alkali or alkaline earth metal hypochlorite and, at least after an initial reaction period, adjusting the pH of the reaction mixture to within the range 9.5 to 11.0 and then maintaining the pH of the reaction mixture within that range by progressive addition of an alkali metal hydroxide.

2. A process according to claim 1 wherein the alkali metal hydroxide is selected from sodium hydroxide and potassium hydroxide.

3. A process according to claim 1 wherein the pH of the reaction mixture is adjusted to and maintained within the range 9.75 to 11.0.

4. A process according to claim 3 wherein the pH of the reaction mixture is adjusted to and maintained within the range 10 to 10.5.

5. A process according to claim 1 wherein, after an initial reaction period, the pH of the reaction mixture is adjusted to within the said range by addition of an inorganic acid.

6. A process according to claim 5 wherein the acid is selected from sulphuric acid and hydrochloric acid.

7. A process according to claim 1 wherein the initial reaction period is within the range 0.5 to 3 minutes.

8. A process according to claim 1 wherein the aqueous organic solvent comprises water and a mixture of tetrahydrofuran and methanol.

9. A process according to claim 1 wherein the hypochlorite comprises sodium hypochlorite.

10. A process for the production of 2,2',4,4',6,6'-hexanitrostilbene according to claim 1 wherein the hypochlorite is added as an aqueous solution having a concentration of free chlorine within the range 4 to 10% (w/v).

11. A process according to claim 1 wherein the reaction is carried out at a temperature within the range $-5°$ to $25°$ C.

12. A process according to claim 1 wherein the reaction is carried out at a temperature within the range $10°$ to $16°$ C.

* * * * *